(12) United States Patent
Narin

(10) Patent No.: US 9,039,598 B2
(45) Date of Patent: May 26, 2015

(54) PENILE RIGIDITY DEVICE

(76) Inventor: Kriangsak Narin, Bangkok (TH)

( * ) Notice: Subject to any disclaimer, the term of this patent is extended or adjusted under 35 U.S.C. 154(b) by 499 days.

(21) Appl. No.: 13/424,445

(22) Filed: Mar. 20, 2012

(65) Prior Publication Data

US 2013/0030244 A1    Jan. 31, 2013

Related U.S. Application Data

(60) Provisional application No. 61/512,811, filed on Jul. 28, 2011.

(51) Int. Cl.
*A61F 5/41*    (2006.01)

(52) U.S. Cl.
CPC ............. *A61F 5/41* (2013.01); *A61F 2005/412* (2013.01); *A61F 2005/415* (2013.01)

(58) Field of Classification Search
CPC   A61F 5/41;  A61F 2005/412;  A61F 2005/415
USPC .................................................... 600/38–41
See application file for complete search history.

(56) References Cited

U.S. PATENT DOCUMENTS

| | | | | |
|---|---|---|---|---|
| 5,947,116 | A * | 9/1999 | Gamow et al. | 128/201.11 |
| 2005/0033113 | A1* | 2/2005 | Bonthuys | 600/38 |
| 2007/0156014 | A1* | 7/2007 | Zafirakis | 600/41 |
| 2008/0269554 | A1* | 10/2008 | Oakes | 600/39 |

* cited by examiner

*Primary Examiner* — Samuel Gilbert
(74) *Attorney, Agent, or Firm* — Joseph Stecewycz

(57) ABSTRACT

Disclosed is penile rigidity device including: a chamber section having a first chamber end and a second chamber end, the chamber section configured as a substantially cylindrical unit having one of a circular or oval cross section; a floating valve section connected to the first chamber end, the valve section configured to allow fluid to selectively flow into and out of the chamber section; and a gaiter section connected to the second chamber end, the gaiter section having a bellows configured to compress in length in response to a pressing force.

18 Claims, 8 Drawing Sheets

PENILE RIGIDITY DEVICE

CROSS REFERENCE TO RELATED APPLICATION

The present Application is related to Provisional Patent Application entitled "Penile Rigidity Device," filed 28 Jul. 2011 and assigned filing No. 61/512,811, incorporated herein by reference in its entirety.

FIELD OF THE INVENTION

The present invention relates to penile rigidity devices and, more particularly, to such devices as may be utilized by general practitioners, specialized penis doctors, and erectile dysfunction specialists.

BACKGROUND OF THE INVENTION

Erection pumps have been known in the art for some years. Operation of such devices includes the steps of placing a chamber over a flaccid penis so as to close the chamber, and using the pump to evacuate the chamber with air or water. This evacuation process causes a pressure differential between the inside and the outside of the chamber, and a corresponding pressure differential between the chamber interior and the blood flow in the penis. As the pressure in the chamber is lowered, additional blood is induced to flow into the penis, and this inflow causes the penis to become more erect.

Conventional erection pumps may include a diagram at a lower end of the chamber, so as to operate via a tube attached at an upper end of the chamber. In a typical application, the tube is connected to a handheld pump device, which is usually in the form of an inflatable bulb with a non-return valve. Such pumps can be modified by enthusiasts to use water rather than air. The user can place the penis through the diagram, into the chamber, and removes air or water from the chamber by use of the pump.

Among the shortcomings with conventional and modern erection pumps are that the erection achieved using such pumps is not very long-lived, and that the erection produced may not be of sufficient rigidity. What is needed is a device which overcomes these, and other, shortcomings of similar devices in the present state of the art.

BRIEF SUMMARY OF THE INVENTION

In one aspect of the present invention, a penile rigidity device comprises: a chamber section having a first chamber end and a second chamber end, the chamber section configured as a substantially cylindrical unit having one of a circular or oval cross section; a floating valve section connected to the first chamber end, the valve section configured to allow fluid to selectively flow into and out of the chamber section; and a gaiter section connected to the second chamber end, the gaiter section having a bellows configured to compress in length in response to a pressing force.

In another aspect of the present invention, a penile rigidity device comprises: a chamber section having a first chamber end and a second chamber end, the chamber section configured as a substantially cylindrical unit having one of a circular or oval cross section; a floating valve section frictionally connected to a first end of the chamber section, the floating valve section including a release pin configured for elastic retention against the second chamber end so as to selectively allow fluid to flow into and out of a valve seat opening in the chamber section; and a gaiter section connected to a second end of the chamber section, the gaiter section having a bellows configured to compress in length when a user presses said penile rigidity device against a lower abdomen, said gaiter section attached to said chamber section by mechanical engagement of an interior circumferential channel disposed in said gaiter section with a circumferential ridge disposed in said chamber section.

In still another aspect of the present invention, a method for inducing an erection in a penis comprises: placing the penis into a penile rigidity device, the penile rigidity device having a chamber section, a gaiter section releasably connected to a first end of the chamber section, and a floating valve section releasably connected to a second end of the chamber section, the floating valve section having a user-operated release pin for selectively allowing fluid to flow into or out of a valve seat opening in the chamber section; pressing said penile rigidity device against a lower abdomen of a user; operating said release pin to allow fluid to pass out of the chamber section; closing the release pin so as to prevent additional fluid from passing out of the chamber section; and releasing the penile rigidity device to cause a decrease in fluid pressure in the chamber section.

The additional features and advantage of the disclosed invention is set forth in the detailed description which follows, and will be apparent to those skilled in the art from the description or recognized by practicing the invention as described, together with the claims and appended drawings.

BRIEF DESCRIPTIONS OF THE DRAWINGS

The foregoing aspects, uses, and advantages of the present invention will be more fully appreciated as the same becomes better understood from the following detailed description of the present invention when viewed in conjunction with the accompanying figures, in which.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention.

The present invention relates generally to a penile rigidity device that provides novel technological innovations, and also utilizes innovative materials and assembly techniques, such that the device can be used while showering, or in a bathtub, under water, or with other liquids. In particular, the present invention comprises a floating valve used to achieve a desirable pressure differential between the inside of the penile rigidity device and the ambient environment. As a result, there is provided a solution which includes: (i) a stronger erection, (ii) a longer lasting erection, and, in some cases (iii) a temporary or permanent cure for erectile dysfunction.

Figure 1:
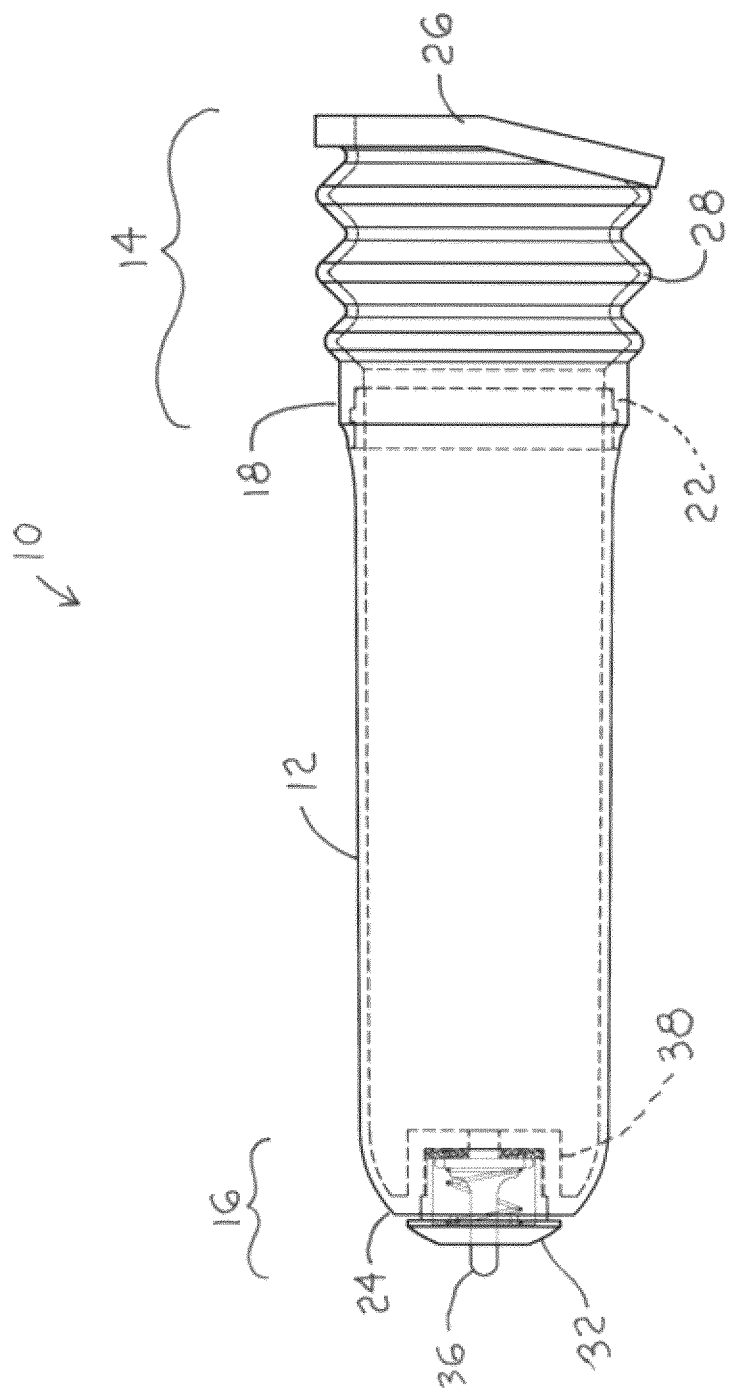
FIG. 1 is a diagrammatical illustration of penile rigidity device, in accordance with the present invention.
Figure 2:
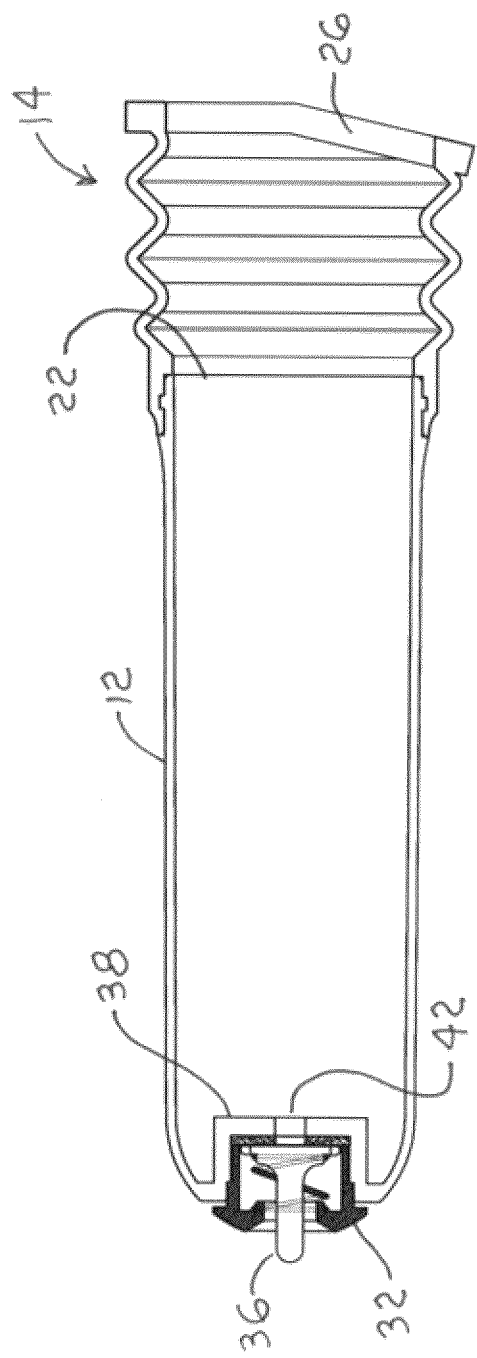
FIG. 2 is a cross sectional diagrammatical view of the penile rigidity device of FIG. 1.
Figure 3:
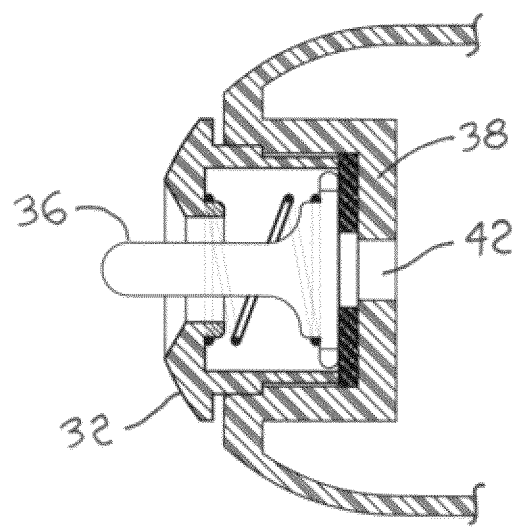
FIG. 3 is a cross-sectional diagrammatical view of a head section of the penile rigidity device of FIG. 1.

There is shown in FIGS. 1 and 2 a penile rigidity device 10 comprising a chamber section 12, a gaiter section 14, and a floating valve section 16. The chamber section 12 may be formed in a substantially cylindrical shape, with a substantially circular or oval cross section, and may be sized to accommodate an erect penis of a user. The gaiter section 14 is secured to a first chamber end 22 of the chamber section 12, and the floating valve section 16 is secured within a second chamber end 24 of the chamber section 12, as described in greater detail below.

The gaiter section 14 is similarly formed in a substantially cylindrical shape, with a substantially circular or oval gaiter mating rim 18 sized to fit over the first chamber end 22. The gaiter mating rim 18 may be retained in place by a friction fit, or may be permanently attached to the chamber section 12 by mechanical attachment means (shown in FIG. 6), by ultrasonic welding or by chemical bonding, as is well known in the relevant art. The gaiter section 14 terminates in a substantially circular or oval gaiter flange 26 that may be anatomically configured to enable sealing of the penile rigidity device 10 against the lower abdomen of the user at the base of the penis when the penile rigidity device 10 is used for its intended purpose.

The flared configuration of the gaiter flange 22 provides for a relatively large annular contact area with the user lower abdomen, and thus may serve to improve the sealing characteristics of the gaiter flange 22 such that the desired pressure inside the penile rigidity device 10 may be maintained. Accordingly, the gaiter section 14 includes a bellows 28 that elastically shortens or contracts in length, by changing from an uncompressed length, or a "free length," to a compressed length, in response to a pressing force. This action of compressing the bellows 28 may occur when a user presses the penile rigidity device 10 against a lower abdomen region. When the pressing force is removed, the bellows 28 elastically expands in length and returns to an extended length. In a typical application, the extended length may be greater than the compressed length of the gaiter section 14, and somewhat less than the free length of the gaiter section 14.

The floating valve section 16 includes a valve cap 32 configured to fit into the second chamber end 24. A release pin 36 protrudes through the valve cap 32 such that the user can operate the penile rigidity device 10, as explained in greater detail below. The second chamber end 24 further includes a valve seat 38 configured to substantially enclose and releasably retain the floating valve section 16 in the second chamber end 14. The valve seat 38 includes a valve seat opening 42 that functions to allow passage a fluid, such as water or air, when the release pin 36 is operated.

The chamber section 12 may comprise a polycarbonate material for increased durability. In an exemplary embodiment, a measurement scale (not shown) may be provided on each side of the chamber section 12, one scale calibrated in inches and the other scale calibrated in centimeters. The chamber section 12 may be provided in a 'smoky clear' configuration or may be tinted in any commercially-available color recognized by a color authority, such as PANTONE. It can be appreciated that either a translucent material or a solid material can be used for the chamber section 12. Additionally, a special coating, such as gold-like or silver-like, may be provided on the inside or outside of the chamber section 12 so as to produce special effects.

Figure 4:
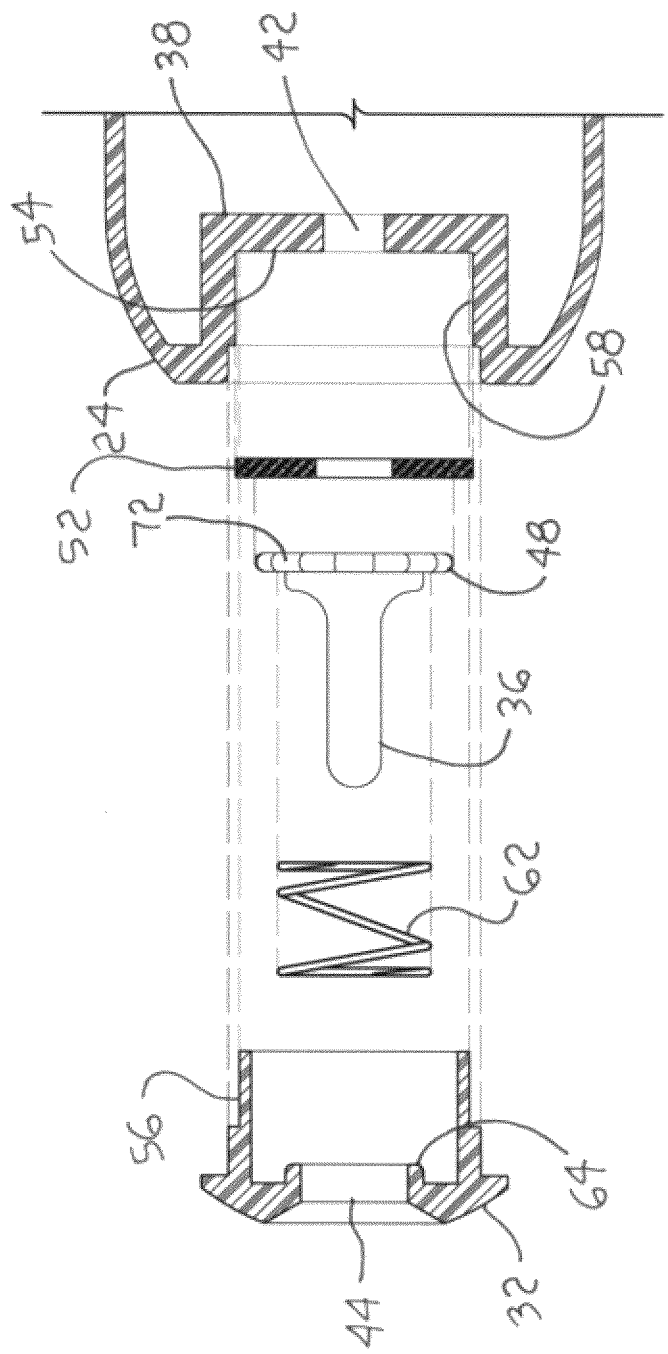
FIG. 4 is an exploded cross-sectional diagrammatical view of the discharge end of the penile rigidity device of FIG. 3.

As further shown in the exploded diagrammatical illustration of FIG. 4, the release pin 36 includes a rounded pin 46 terminating in a flared pin base 48. The valve cap 32 includes a cap opening 44 sized to allow the rounded pin 41 to be tilted and moved side-to-side within the cap opening 44. The flared pin base 48 may be elastically disposed against an O-ring 52 by means of a compression spring 62. The O-ring 52 may be placed against a sealing surface 54 of the valve seat 38 during normal operation of the penile rigidity device 10. In an exemplary embodiment, the O-ring 52 is formed from natural rubber or a medical grade silicone-based material.

The valve cap 32 further includes a cap wall 56 that is sized to fit into, and be releasable retained within, the valve seat 38. In an exemplary embodiment, the valve cap 32 may be retained in the valve seat 38 by a frictional fit, or attached to the valve seat 38 by ultrasonic welding or by chemical bonding. The compression spring 52 may be disposed between the valve cap 32 and the flared pin base 48 so at to forcibly retain the flared pin base 48 against the sealing surface 54, as described above. In an exemplary embodiment, the compression spring may be formed from stainless steel, and be designed with a relatively low spring rate. The valve cap 32 may further include a cap mesa 64 sized and positioned to retain the compression spring 62 in a desired position against the valve cap 32.

Figure 5:
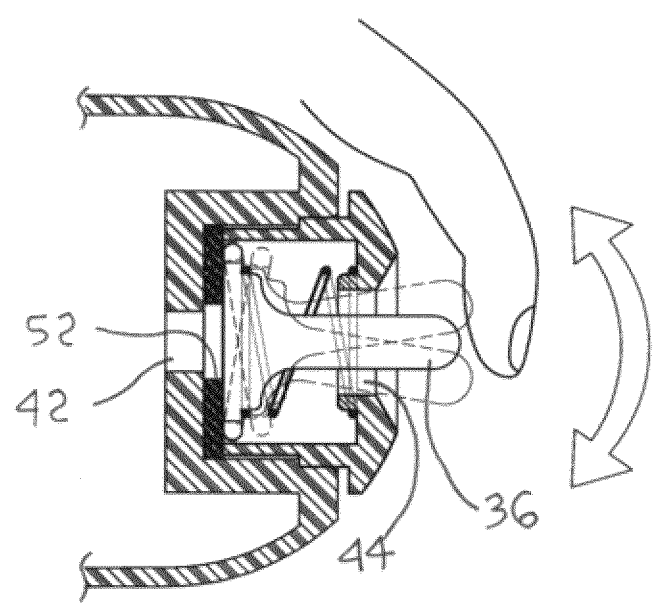
FIG. 5 is an cross-sectional diagrammatical view illustrating operation of a pin in the discharge end of the penile rigidity device of FIG. 3.

When the release pin 36 is tilted, side-to-side, within the cap opening 44, as shown in FIG. 5, fluid may pass through the valve seat opening 42 and through the O-ring 52. It can be appreciated that, as the release pin 36 functions as a "floating valve," fluid can flow in either direction when the release pin 36 is operated by the user. That is, when the fluid pressure inside the chamber section 12 is higher than the ambient pressure on the outside of the chamber section 12, fluid in the chamber 12 will pass out through the floating valve section 16 when the when the release pin 36 is operated by the user.

Conversely, when the fluid pressure inside the chamber section 12 is lower than the ambient pressure on the outside of the chamber section 12, fluid will pass into the chamber 12 through the floating valve section 16 when the when the release pin 36 is operated. The flared pin base 48 may include a plurality of grooves 72 formed in the outer rim of the flared pin base 48, where the grooves function to improve the flow of fluid into and out of the valve seat opening 42. In an exemplary embodiment, the flared base may include eight grooves 72, substantially equally spaced around the outer rim of the flared pin base 48.

Figure 6:
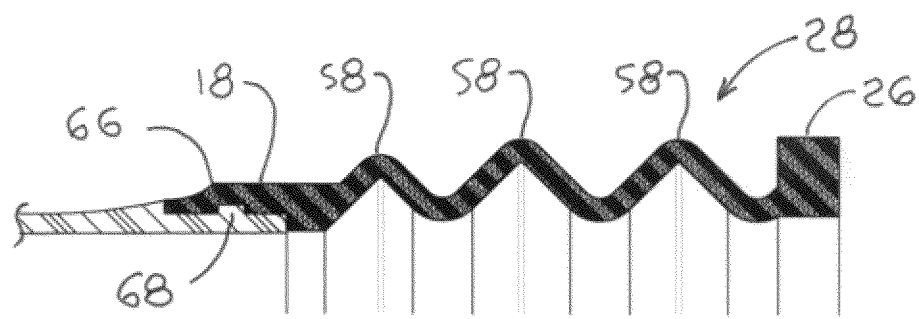
FIG. 6 is a cross-sectional view diagrammatical view of a base section of the penile rigidity device of FIG. 1.

As can be seen in the diagrammatical cross sectional view of FIG. 6, the bellows 28 may be fabricated from a flexible, waterproof, medical-grade silicone compound and may comprise a plurality of convolutions or ridges 58 designed for flexure. In an exemplary embodiment, the bellows 28 may comprise three or more rounded ridges 28, having substantially triangular or sinusoidal shapes, for ease in compression and expansion of the bellows 28. This attribute advantageously enhances operation of the penile rigidity device 10.

In an exemplary embodiment, the gaiter mating rim 18 may include an interior circumferential channel 66 configured to mate with a circumferential ridge 68 on the first chamber end 22 of the chamber section 12. The gaiter section 14 may thus be releasable mated to and removed from the chamber section 12, as desired by the user. The gaiter flange 26 may be approximately 0.6 to 1.2 cm in thickness to maximize contact with the lower abdomen of the user and enhance the sealing ability of the gaiter flange 26.

Figure 7:
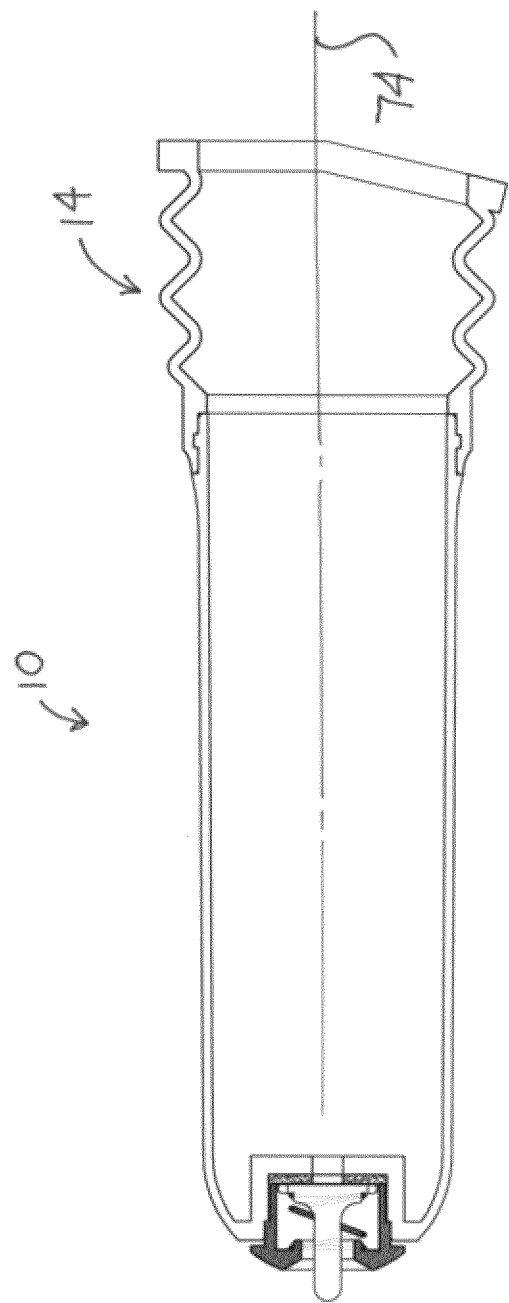
FIG. 7 is a cross-sectional diagrammatical view of the penile rigidity device of FIG. 3 in a non-compress mode.
Figure 8:
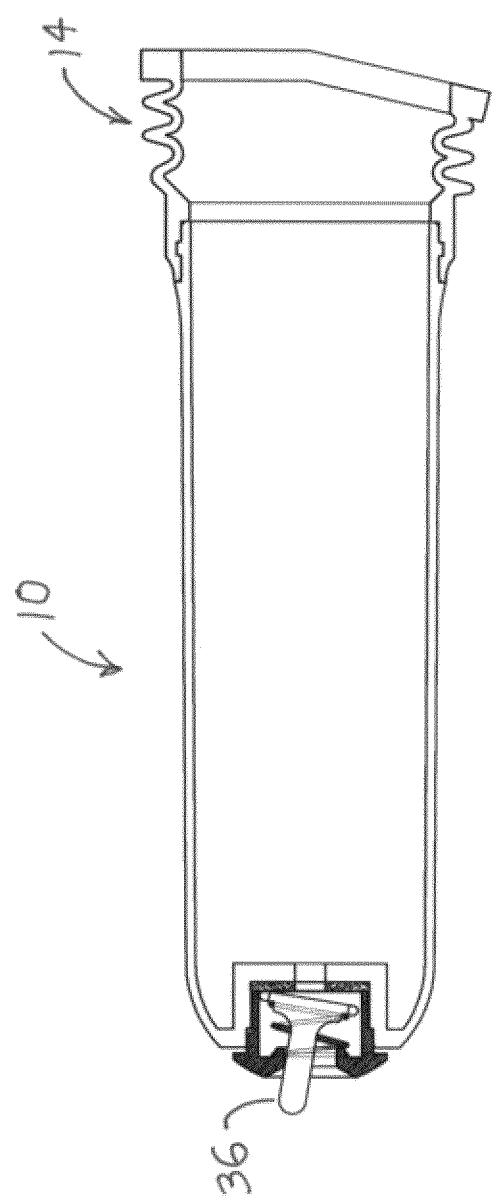
FIG. 8 is a cross-sectional diagrammatical view of the penile rigidity device of FIG. 3 in a semi-compress mode; and, FIG. 9 is a cross-sectional diagrammatical view of the penile rigidity device of FIG. 3 in a full-compress mode.
Figure 9:
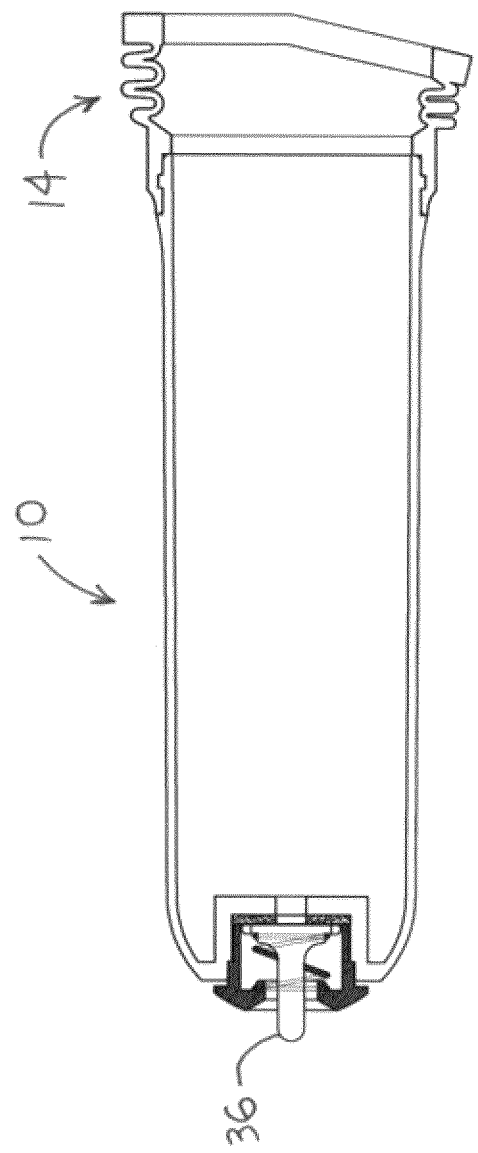

Operation of the penile rigidity device 10 can be explained with reference to FIGS. 7-9 in which the user obtains the penile rigidity device 10 in which the gaiter section 14 is in a non-compressed state, or free length, shown in FIG. 7. The chamber section 12 and the gaiter section 14 may contain a fluid (not shown), such as water. The penile rigidity device 10 is then placed over the penis of the user, and the penile rigidity device 10 is forced against the lower abdomen of the user such that the gaiter section 14 is compressed in length, as shown in FIG. 8. It can be appreciated by one skilled in the relevant art that the user applies a compressive force along a longitudinal axis 74 of the penile rigidity device 10 so as to compress the gaiter section 14. Preferably, the release pin 36 is actuated so as to allow some of the fluid in the chamber section 12 to escape from the penile rigidity device 10.

When the length of the gaiter section 14 is substantially fully compressed, as shown in FIG. 8, the release pin 36 is moved back to a position in which the compression spring 62 forces the flared pin base 48 to dose off the valve seat opening 42. The user may subsequently allow the gaiter section 14 to expand somewhat, lengthening the bellows 28, and causing the pressure in the chamber section 12 to decrease. This action causes the penis to increase in rigidity, producing or increasing a state of erection. The previous steps, of compressing and lengthening the bellows 28, and operating the release pin 36, may be repeated, as desired by the user.

When the length and state of the penis has reached a desired state, the user may operate the release pin 36 to release fluid from the penile rigidity device 10 and lower the fluid pressure in the chamber section 12. This action then allows the user to remove the penile rigidity device 10 from the penis, and leave the penis in the desired state.

In the configuration shown in FIG. 1, the bellows 28 includes three convolutions or ridges 58 to provide a bellows spring rate sufficiently large such that the length of the bellows 28 increases—from a first shorter length to a second longer length—when the wearer of the user decreases the pressing force and allows the gaiter section 14 to expand or uncompress. It can be appreciated by one skilled in the art that the bellows 28 may include more or fewer than the three convolutions or ridges 58 shown, the optimal number of convolutions or ridges 58 required depending upon the material used for the gaiter section 14, the overall uncontracted length of the gaiter section 14, and the thickness of the wall of the bellows 28.

It is to be understood that the description herein is exemplary of the invention only and is intended to provide an overview for the understanding of the nature and character of the disclosed illumination systems. The accompanying drawings are included to provide a further understanding of various features and embodiments of the method and devices of the invention which, together with their description serve to explain the principles and operation of the invention.

What is claimed is:

1. A penile rigidity device comprising:
    a chamber section having a first chamber end and a second chamber end, said chamber section configured as a substantially cylindrical unit having one of a circular or oval cross section;
    a floating valve section connected to said first chamber end, said valve section configured to allow fluid to selectively flow into and out of said chamber section, said floating valve section including a release pin having a flared pin base, said flared pin base elastically disposed against a valve seat opening in said valve seat, said flared pin base including a plurality of grooves substantially equally spaced around an outer rim of said flared pin base; and
    a gaiter section connected to said second chamber end, said gaiter section having a bellows configured to compress in length in response to a pressing force.

2. The penile rigidity device of claim 1 wherein said chamber section further comprises a circumferential ridge in said first end for releasably retaining said gaiter section.

3. The penile rigidity device of claim 1 wherein said gaiter section is attached to said chamber section by at least one of: mechanical attachment means, ultrasonic welding, and chemical bonding.

4. The penile rigidity device of claim 3 wherein said mechanical attachment means comprises an interior circumferential channel disposed in said gaiter section and a circumferential ridge disposed in said chamber section.

5. The penile rigidity device of claim 1 wherein said chamber section further comprises a valve seat in said second end for releasably retaining said floating valve section.

6. The penile rigidity device of claim 1 wherein said floating valve section is attached to said chamber section by at least one of: a frictional fit, ultrasonic welding, and chemical bonding.

7. The penile rigidity device of claim 1 further comprising a compression spring disposed to forcibly retain said flared pin base against said valve seat opening.

8. The penile rigidity device of claim 1 wherein said floating valve section comprises a valve cap, said valve cap including a valve cap opening, said valve cap opening positioned to allow said release pin to extend through said valve cap opening, said valve cap opening further sized to allow said release pin to be tilted by a user.

9. The penile rigidity device of claim 1 wherein said floating valve section comprises an O-ring disposed against said first chamber end.

10. The penile rigidity device of claim 1 wherein said gaiter section comprises a bellows, said bellows compressing in response to a user pressing said penile rigidity device against an abdomen region.

11. A penile rigidity device comprising:
    a chamber section having a first chamber end and a second chamber end, said chamber section configured as a substantially cylindrical unit having one of a circular or oval cross section;
    a floating valve section frictionally connected to a first end of said chamber section, said floating valve section including a release pin configured for elastic retention against said second chamber end so as to selectively allow fluid to flow into and out of a valve seat opening in said chamber section, said release pin including a flared pin base, said flared pin base including a plurality of grooves substantially equally spaced around an outer rim of said flared pin base; and
    a gaiter section connected to a second end of said chamber section, said gaiter section having a bellows configured to compress in length when a user presses said penile rigidity device against a lower abdomen, said gaiter section attached to said chamber section by mechanical engagement of an interior circumferential channel disposed in said gaiter section with a circumferential ridge disposed in said chamber section.

12. The penile rigidity device of claim 11 wherein said chamber section comprises a valve seat configured to substantially enclose said floating valve section.

13. The penile rigidity device of claim 11 wherein said bellows comprise a plurality of convolutions, each said convolution having at least one of a sinusoidal and a triangular cross sectional configuration.

14. A method of inducing an erection in a penis, said method comprising the steps of:
- placing the penis into a penile rigidity device, said penile rigidity device having a chamber section, a gaiter section releasably connected to a first end of said chamber section, and a floating valve section releasably connected to a second end of said chamber section, said floating valve section having a user-operated release pin for selectively allowing fluid to flow into or out of a valve seat opening in said chamber section; said release pin including a flared pin base, said flared pin base including a plurality of grooves substantially equally spaced around an outer rim of said flared pin base;
- operating said release pin to allow fluid to pass through said chamber section;
- pressing said penile rigidity device against a lower abdomen of a user so as to decrease the length of said gaiter section to a compressed length;
- closing said release pin so as to prevent additional fluid from passing through said chamber section; and
- terminating said step of pressing said penile rigidity device, whereby fluid pressure in said chamber section is thereby decreased.

15. The method of claim 14 further comprising the step of repeating said steps of: operating said release pin and pressing said penile rigidity device against said lower abdomen.

16. The method of claim 14 wherein said step of terminating said step of pressing comprises the step of allowing the length of said gaiter section to increase from a first shorter length to a second longer length.

17. The method of claim 14 wherein said step of pressing said penile rigidity device comprises the step of applying a compressive force along a longitudinal axis of said penile rigidity device.

18. The method of claim 14 further comprising the steps of:
- operating said release pin to allow fluid to pass through said chamber section; and
- removing said penile rigidity device from the penis.

* * * * *